US008557587B2

(12) United States Patent
Fox et al.

(10) Patent No.: US 8,557,587 B2
(45) Date of Patent: Oct. 15, 2013

(54) SELF-TUNING, BIOLOGICALLY MODELED SORTER

(75) Inventors: Daniel N. Fox, Fort Collins, CO (US); George C. Malachowski, Melbourne (AU); Matthias J. G. Ottenberg, Holmen, WI (US); Tidhar Sadeh, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 663 days.

(21) Appl. No.: 12/683,395

(22) Filed: Jan. 6, 2010

(65) Prior Publication Data
US 2011/0010144 A1    Jan. 13, 2011

Related U.S. Application Data

(60) Provisional application No. 61/142,926, filed on Jan. 7, 2009.

(51) Int. Cl.
*G01N 31/00*    (2006.01)
*G01N 33/00*    (2006.01)
(52) U.S. Cl.
USPC ................ 436/10; 422/73; 702/21; 702/26; 702/46; 702/128; 703/2

(58) Field of Classification Search
USPC ............ 422/73; 436/10; 702/21, 26, 46, 128; 703/2
See application file for complete search history.

(56) References Cited

U.S. PATENT DOCUMENTS

| 2004/0029213 | A1* | 2/2004 | Callahan et al. ............ 435/40.5 |
| 2005/0112541 | A1* | 5/2005 | Durack et al. .................... 435/2 |
| 2006/0257013 | A1 | 11/2006 | Ramm et al. | |
| 2008/0255705 | A1 | 10/2008 | Degeal et al. | |

OTHER PUBLICATIONS

U.S. Appl. No. 61/142,926, filed Jan. 7, 2009.

* cited by examiner

*Primary Examiner* — Dean Kwak
(74) *Attorney, Agent, or Firm* — William W. Cochran; Cochran Freund & Young LLC (57) ABSTRACT

Disclosed is a self-tuning flow cytometer that uses a mathematical model to perform sort decisions that is based upon the biological response of the particular types of cells that are being sorted. In one embodiment, statistical calculations of the likelihood of an event belonging to a certain population are used to make the sort decisions. Automated self-tuning processes are used to optimize the operating parameters of the flow cytometer to achieve a selected purity with higher yield at optimal sorting speeds. The fully automated processes minimize user input and allows the user to select a desired purity while maximizing yield.

9 Claims, 6 Drawing Sheets

SELF-TUNING, BIOLOGICALLY MODELED SORTER

CROSS-REFERENCE TO RELATED APPLICATION

This application claims benefit of and priority to U.S. Provisional Patent Application Ser. No. 61/142,926, entitled "Self-Tuning, Biologically Modeled Sorter" by Daniel N. Fox, et al., filed Jan. 7, 2009, the entire contents of which are specifically incorporated herein by reference for all that they disclose and teach.

BACKGROUND OF THE INVENTION

Flow cytometry has historically been performed with general purpose instruments designed to allow for a wide range of applications. Flow cytometers function by passing cells in a single file line, under ideal circumstances, through one or more laser interrogation points. Scattered and/or emitted light is then collected and filtered at specific wavelengths and converted to an electrical signal representative of the intensity of the light at those specific wavelengths. The properties of the detected signal are measured and information regarding the cell is used to make a sort decision. User selected criteria is utilized to make a sort decision. The user selected criteria defines gates for selection of events within a histogram. Complex logic, including multiple parameters and histograms, additional regions and gates and cascaded gates allow users to specify which cells are to be sorted. This process of user defined regions to perform sorting processes is referred to as region classification. In that regard, if an event (a cell) falls within one or more regions and, in some cases, in or not in other regions on a histogram, sort logic is used to determine cells of interest.

SUMMARY OF THE INVENTION

The present invention may therefore comprise a method of sorting a plurality of cells in a flow cytometer comprising: generating a mathematical model that is based upon biological responses of the cells to illumination by a source of electromagnetic radiation in the flow cytometer; calculating event probability data using the mathematical model that a cell of the plurality of cells belongs to a predetermined population; calculating droplet probability data by comparing a location of the cell in a predetermined droplet with a probability table; calculating droplet desirability data for the predetermined droplet by combining the event probability data and the droplet probability data; calculating a sort decision signal by comparing the droplet desirability with a predetermined threshold that is set to achieve a desired purity.

The present invention may further comprise sorting logic for a flow cytometer that sorts cells based upon an optical response of the cells to illumination by a source of electromagnetic radiation comprising: an event probability calculator that uses a mathematical model to calculate event probability data for each cell that indicates whether the cell belongs to a predetermined population; a droplet probability calculator that compares a location of the cell in a predetermined droplet with a probability table to produce droplet probability data that the cell is present in the predetermined droplet; a droplet desirability calculator that combines the event probability data and the droplet probability data to produce droplet desirability data; a sort decision calculator that compares the droplet desirability data with a predetermined threshold to produce a sort decision signal that is used by the flow cytometer to sort the cells.

The present invention may further comprise a method of sorting a plurality of cells in a flow cytometer comprising: generating a mathematical model that is based upon biological responses of the cells to illumination by a source of electromagnetic radiation in the flow cytometer; calculating event probability data using the mathematical model that a cell of the plurality of cells belongs to a predetermined population; calculating droplet desirability data for the predetermined droplet from the event probability data; calculating a sort decision signal by comparing the droplet desirability with a predetermined threshold that is set to achieve a desired purity.

The present invention may further comprise sorting logic for a flow cytometer that sorts cells based upon an optical response of the cells to illumination by a source of electromagnetic radiation comprising: an event probability calculator that uses a mathematical model to calculate event probability data for each cell that indicates whether the cell belongs to a predetermined population; a droplet desirability calculator that uses the event probability data to produce droplet desirability data; a sort decision calculator that compares the droplet desirability data with a predetermined threshold to produce a sort decision signal that is used by the flow cytometer to sort the cells.

DETAILED DESCRIPTION OF EMBODIMENTS OF THE INVENTION

Figure 1:
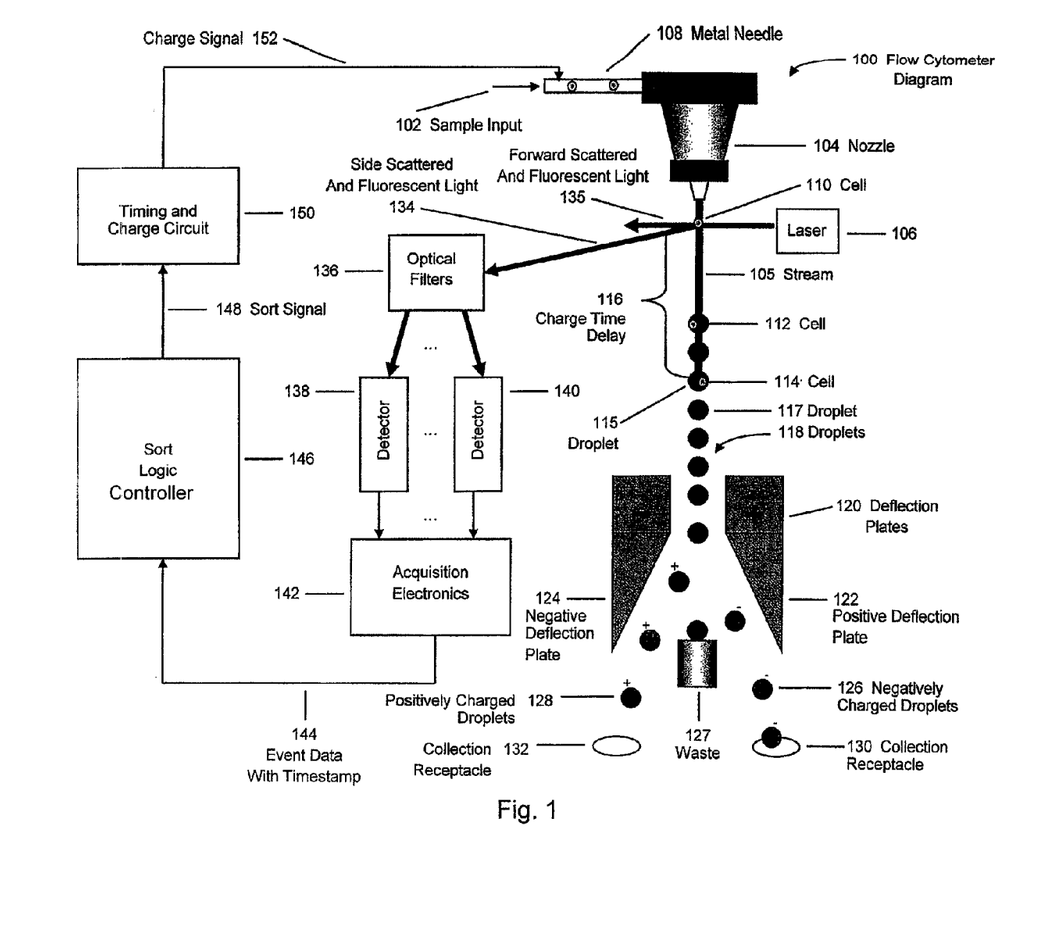
FIG. 1 is a schematic diagram of an embodiment of a flow cytometer.

FIG. 1 is a schematic diagram illustrating one embodiment of a flow cytometer 100. As illustrated in FIG. 1, a sample 102 is inserted into an input of the nozzle 104. The sample may comprise many different types of objects to be sorted, including blood cells, bacteria, microorganisms, or any other type of cell or particle. In one embodiment, bull sperm is sorted based upon the DNA content of the sperm. In addition, sperm cells from any animal can be sorted based upon the DNA content of the sperm.

Typical flow cytometers use region classification that separates cells, such as by employing user defined regions on bivariate histograms. User defined logic is employed to perform the sort operations. Boolean logic may be used when multiple regions are defined, so as to select cells that may be included in one or more regions and excluded from one or more other regions. Using this approach, marginal events that fall just outside of a region are ignored as a result of the clear delineation of these regions that are defined by the user. In some situations, this can lower yield of the overall process, which is an important factor in commercial implementation of various technologies, including the sorting of bull sperm, or other types of sperm. Other problems, such as the presence of multiple cells in single droplets, may also reduce yield, since the logic that defines the highly delineated regions will not select these droplets if one of the cells falls slightly outside of a region, as explained in more detail below.

In addition, region classification for sorting may cause problems in obtaining a desired purity of the sorted cells. As one example, a general purpose flow cytometer is operated to sort particular types of cells, such as bull sperm, or other types of sperm. The user analyzes the data generated to identify cells of interest. The user then develops a gating scheme, so that the instrument sorts the desired cells. However, the sorted output is only as good as the criteria used to select these cells. If the desired cells are difficult to fully specify, such as cells that have a response that is overlapping with an undesired population, even small changes in the selection criteria, i.e., the delineated regions, can greatly impact the performance of the general purpose flow cytometer. In the particular example of sorting bull sperm, the industry has adopted a cost/benefit ratio that utilizes 90% purity in the sorted samples as an established criterion. There is no way of effectively selecting a user defined region to produce 90% purity by simply analyzing the histogram, especially for overlapping populations. Typically, many iterations must be performed to set the region properly. This iterative process is performed by investigating the actual output to achieve the desired purity and yield. For example, if the response of a desired population overlaps with an undesired population, using traditional techniques, the user must delineate the region between the two populations for selection of the desired events. In other words, a line must be drawn between the two overlapping populations to delineate the selection of the desired cells from the undesired cells. If a certain purity is desired, an iterative process must be employed by analyzing the empirical results and redefining the user defined regions to achieve the desired purity. This is a time consuming process that frequently results in wasted sample and time. In other words, the use of gated logic to define user defined regions does not allow for upfront selection of purity and yield, which are important factors in commercial processes, such as the processing of bull sperm, or other types of sperm, and may cause the flow cytometer to operate suboptimally.

Further, if the population of a desired event overlaps with the population of undesired events, slight variations in the delineation of the regions between the overlapping populations can result in large variations in purity, as explained in more detail below. In that regard, changes in the various operating parameters of a flow cytometer can have the same effect. For example, a change in the room temperature can cause the operating parameters of the cytometer to shift, which has the same effect as shifting the user defined regions. A shift in temperature can affect the fluidics of the stream, the optics, the mirrors, the steering stages, and can move the laser beam, so that the peak intensity of the laser beam is no longer aligned with the fluidic stream. Changes in room temperature can also affect the photomultiplier tube gain slightly, so that the electronic response may be either diminished or increased for the same optical signal. The electronics may also be affected. The resistance of resistors in the flow cytometry circuitry changes with temperature. Since different portions of the flow cytometer have different temperature coefficients, one resistor may change more than another, causing the gain to change slightly. As set forth above, there are many portions of the flow cytometer which can change slightly that cause large changes in purity and yield of the flow cytometer, especially when overlapping populations are being sorted. Hence, typical flow cytometers are extremely sensitive to slight changes and to the criteria of user selected regions.

Referring again to FIG. 1, the sample 102 is sent through the nozzle 104 under pressurized conditions and creates a stream 105 at the output of the nozzle 104. The stream 105 breaks off into a series of droplets 118. Laser 106 irradiates cells within the sample, such as cell 110. Depending upon the type of cell that is irradiated by the laser 106, the cell will generate an optical response. The optical response may be forward scattered light or forward fluorescent emissions 135. Alternatively, or in addition, the response of the cell 110 to the irradiation by laser 106 may be side-scattered light, or side fluorescent emissions 134. These responses are transmitted through optical filters 136 to detectors 138, 140, which typically comprise photomultiplier tubes. The sample fluid 102 progresses at an even rate from nozzle 104 to generate substantially evenly spaced droplets 118. The cells, however, within the sample fluid, progress at an uneven rate. As a result, some droplets will not contain any cells, while other droplets will contain multiple cells. In typical flow cytometers, if a droplet contains more than one cell, and if one cell in the droplet constitutes a desired event, and the other cell within the droplet is slightly outside of the user selected region, the droplet will not be sorted. This process significantly negatively impacts yield of the process, especially if there are overlapping regions of the two populations. Hence, there are a number of factors that affect the sorting process in flow cytometers.

Referring again to FIG. 1, the detectors 138, 140 generate output signals that have a magnitude that is indicative of the intensity of the light collected from the cell 110, at the specific frequencies of the optical filters 136. The acquisition electronics generates an event data signal 144 that has a time stamp to identify the data with a particular cell. The event data signal 144 is applied to the sort logic 146. As described in more detail below, sort logic 146 uses a mathematical model to perform sort decisions that are based upon the biological response of the particular types of cells that are being sorted. In one embodiment, statistical calculations of the likelihood of an event belonging to a certain population are used for making the sort decision.

The sort signal 148 at the output of the sort logic 146 is applied to the timing and charge circuitry 150. The timing and charge circuitry 150 generates a charge signal 152 in response to the sort signal 148 at the proper time to charge a droplet, such as droplet 115, just prior to breaking off from the stream 105. The charge signal 152 is applied to the metal needle 108 that is in contact with the stream 105 to charge the stream 105 to a voltage level, so that when a droplet, such as droplet 117, breaks off from the stream 105, the droplet 117 is charged. The timing portion of the timing and charge circuit 150 generates the charge signal 115 just prior to the time that a droplet, such as droplet 115, breaks off from the stream 105.

As further illustrated in FIG. 1, the droplets 118 travel between deflection plates 120. The positive deflection plate 122 and negative deflection plate 124 create a static electromagnetic field that diverts the negatively charged droplets 126 to collection receptacle 130 and the positively charged droplets 128 to collection receptacle 132. Droplets that are not charged fall into waste receptacle 127. In this manner, the flow cytometer 100 is capable of separating the droplets in accordance with the sort logic 146.

Figure 2:
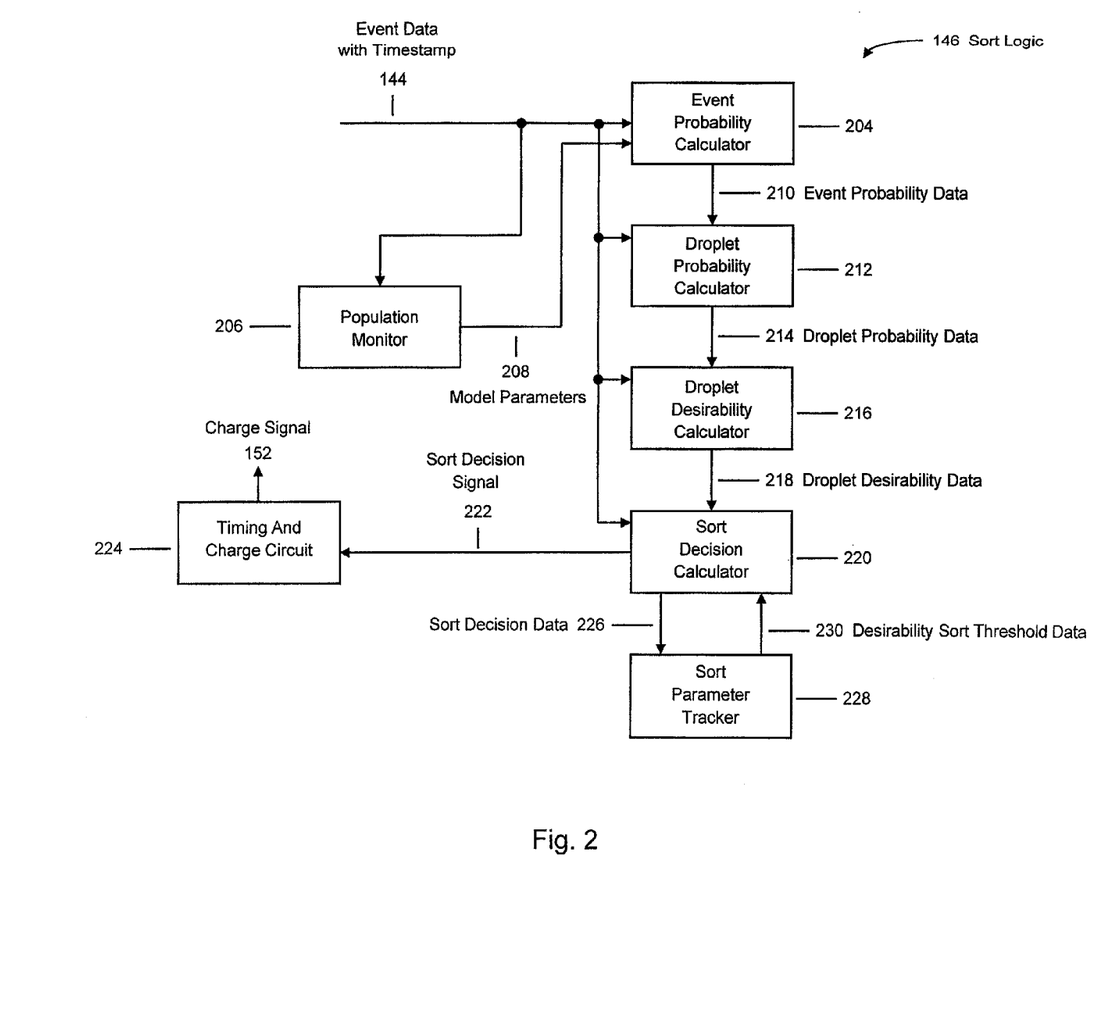
FIG. 2 is a schematic block diagram of the sort logic.
Figure 3:
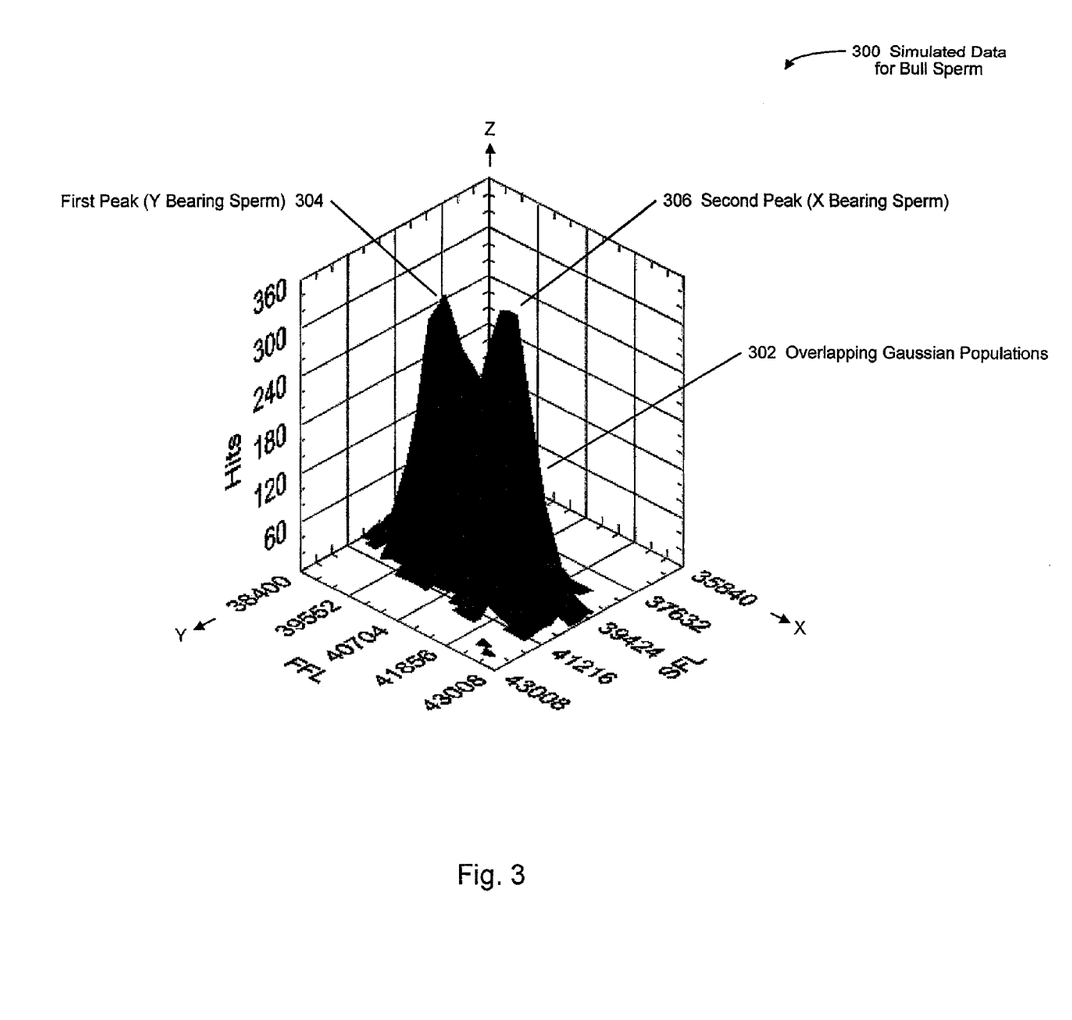
FIG. 3 is a three-dimensional graph of a histogram with overlapping Gaussian populations.

FIG. 2 is a detailed schematic block diagram of one embodiment of the sort logic 146. As shown in FIG. 2, the event data 144 that has been time stamped is applied to an event probability calculator 204. The event probability calculator calculates the probabilities for each event that the event belongs to a certain population. The event probability calculator 204 is designed to use a mathematical model for a particular biological application so that data that is collected during operation of the flow cytometer 100 can be analyzed in accordance with that mathematical model. In accordance with one embodiment, data collected from bull sperm, and other types of sperm, results in two overlapping Gaussian populations, such as illustrated in FIG. 3. FIG. 3 constitutes simulated data for bull sperm showing a three-dimensional bivariate histogram with overlapping Gaussian populations 302. A first peak 304 represents the data for Y-bearing sperm. The second peak 306 indicates data for X-bearing sperm. FIG. 3 is a plot of the forward fluorescence in the X direction plotted against the side fluorescence in the Y direction, versus the number of data points or hits in the Z direction. Other types of sperm may have a similar response. In that regard, the techniques used herein can be used with other types of sperm, or other types of cells, that have overlapping Gaussian population distributions. The description of the separation of bull sperm is for illustrative purposes since the described techniques are applicable to any cells that create responses that are overlapping probability distributions or allow the creation of other mathematical models.

As also shown in FIG. 3, the first peak 304 and the second peak 306 show a clear delineation for separating cells. However, there is a large overlapping area 302 between the two peaks 304, 306. The simulated data of FIG. 3 is very similar to two overlapping Gaussian curves. Hence, standard statistical methods can be used to analyze probabilities of events belonging to each of the Gaussian curves, or other probability distributions. Gaussian distributions are described herein for illustrative purposes only, and any type of probability distribution can be used to build a mathematical model. Initially, the two Gaussian curves, represented by peaks 304, 306, can be mathematically deconvolved to build the mathematical model of the biological response illustrated in FIG. 3. After the two curves are deconvolved, a Gaussian model of each separate population of events can be generated. Once the biological response of each of the separate populations is modeled by Gaussian curves, the mean ($\mu$) and standard deviation ($\sigma$) can be calculated to determine the probability of any particular event belonging to one or the other of the population of events. One way of determining whether a particular event belongs to one or the other Gaussian populations is to use the normal population probability density function (PDF), which is given as:

$$\frac{1}{\sigma\sqrt{2\pi}}\exp\left(-\frac{(x-\mu)^2}{2\sigma^2}\right) \quad \text{Equation 1}$$

Where a $\sigma$=standard deviation, $\mu$=mean and $\chi$ is two-dimensional the value of the event. Hence, the value ($\chi-\mu$) is the distance of the event from the mean.

The event probability calculator 204, as illustrated in FIG. 2, also includes a calculator for calculating the most likely population (MLP) to which an event belongs. As shown in FIG. 3, each event has an x coordinate, which is indicative of the intensity of the forward fluorescence that was detected by a detector in the flow cytometer, and a y coordinate, which is indicative of the intensity of the side fluorescence that was detected by one of the detectors in the flow cytometer. The variable $\chi$ in the event probability equation (Equation 1) is the xy value of each event. To calculate the probability that an event belongs to a first population (PDF1), the value for $\chi$ of that event is entered in the PDF equation (Equation 1), together with the value of the mean ($\mu$) for the first population and the value of the standard deviation ($\sigma$) of the Gaussian distribution for the first population. The probability density function (PDF2) for that same event for the Gaussian distribution of the second population is calculated by entering the same value for $\chi$ and the mean ($\mu$) and standard deviation ($\sigma$) for the Gaussian distribution of the second population. To determine the most likely population (MLP) that a particular event may belong to, the following calculations can be made: (MLP) PDF1/(PDF1±PDF2). MLP2=PDF2/(PDF1±PDF2). MLP1 is a calculated number that indicates the likelihood that a particular event belongs to a first population of events. MLP2 is a calculated number that indicates the likelihood that a particular event belongs to a second population. By comparing MLP1 with MLP2, the likelihood that an event belongs to a particular population can be easily determined by determining which is the larger number.

However, the event probability calculator 204 of FIG. 2 must also determine whether the event has a likelihood of belonging to that most likely population that was previously calculated. In that regard, an errant event may indicate a high probability of being located in a particular population, but may not even fall within the Gaussian distribution for that population. Hence, an additional calculation can be made to determine the likelihood as to whether that event has a likelihood of belonging to the most likely population. The first step in this process is to calculate a maximum likelihood (MLH) number, which is a calculation of the PDF with ($\chi-\mu$) =0. The number calculated for the PDF of the event for the most likely population (MLP) is then divided by MLH to determine the percentage probability that the event belongs to that population. In other words, if it was determined that the most likely population was population 1, then PDF1 would be divided by MLH to give the probability of the event belonging to population 1. Stated differently, the percentage probability that an event belongs to a most likely population (PMLP) is PMLP=PDF1/MLH. An example is given below:

TABLE 1

| Population: | 1 | 2 |
|---|---|---|
| Mean: | (146, 146) | (100, 100) |
| Standard Deviation: | 33 | 33 |
| Event 2D location: | (190, 170) | |
| PDF Output Pop 1 (PDF1): | 0.007638279 | |
| PDF Output Pop 2 (PDF2): | 0.000030916 | |
| Ratio Pop 1 to Sum (MLP1): | 0.9960 | |
| Ratio Pop 1 only (PMLP): | 0.6318 | |

This example indicates that the event, which is located at (190, 170) is 99.6% likely to belong to the first population rather than the second population. In addition, this example illustrates that there is a 63.18% chance that the event is part of the first population.

Of course, the above calculations are only one example of the manner in which these probabilities may be calculated. For example, determination of whether a particular event is more likely to belong to a particular population can be simply done by taking the ratios of the distances of the event from the mean of each population. Further, mathematical models can be established for a wide variety of biological responses. For example, sorting of three different types of cells may result in a biological model that indicates three overlapping Gaussian responses. Further, other probability functions can be used if the biological response does not produce a Gaussian output. In some cases using lookup tables instead of probability functions or other methods entirely may have merit.

Referring again to FIG. 2, the event data 144 is monitored by population monitor 206, as the data is being generated, to track changes in the mean ($\mu$) and the standard deviation ($\sigma$). In this manner, shifts or changes in the sample, or the flow cytometer, will cause the calculation of the event probability to also shift in an automatic fashion to ensure that the selection criteria using the probability information is correct. Recalculation of the mean (μ) and standard deviation (σ) can be performed by population monitor 206 upon receipt of each additional data point, or after a preset number of data points are received. For example, the mean (μ) and standard deviation (σ) may be recalculated after every 500, 1,000 data points, or other number of data points are generated. As shown in FIG. 2, the model parameters 208, such as the mean and standard deviation, are then provided to the event probability calculator to continuously update the event probability. Further, the mathematical model can be initially established and the flow cytometer operated with actual data points to populate the mathematical model and ensure that the mathematical model is adjusted properly to reflect the data. This can be done without sorting and with the sample re-run after the mathematical model is established to sort the sample.

Figure 4:
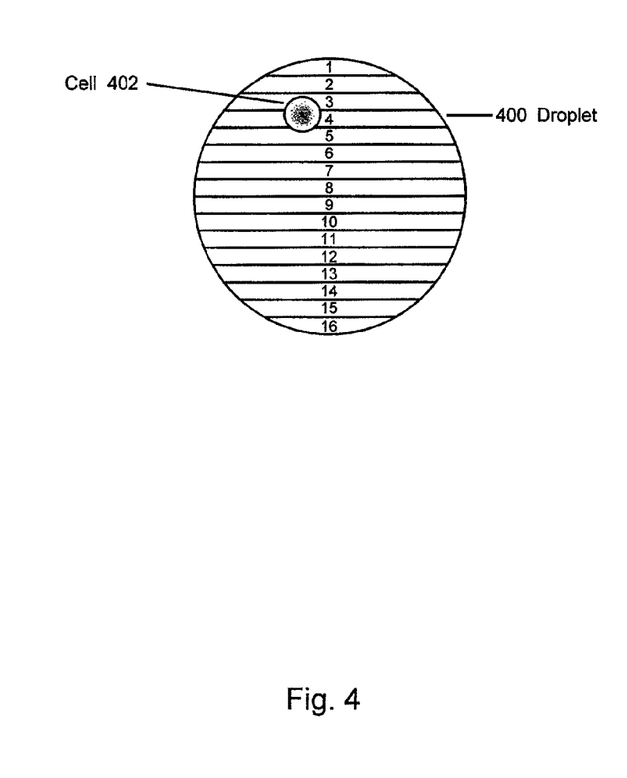
FIG. 4 is a schematic illustration of a cell within a droplet.

Once the event probability data 210 has been calculated, the droplet probability data 214 for each event is calculated by droplet probability calculator 210. The probability that an event will be included in the next droplet, such as droplet 115, that separates from the stream 105 is calculated by the droplet probability calculator 210. FIG. 4 is a schematic illustration of a droplet 400 containing a cell (event) 402 that is disposed in a location in the droplet 400, just before the droplet separates from the stream 115. Depending upon the location of an event within the droplet 400, the event can be assigned a probability of actually ending up in the droplet. Events that are positioned near droplet boundaries have a probability that is split between the next expected droplet and the following droplet. Empirical data can be collected for the operation of the flow cytometer, and the presence of events in droplets, to build a probability table that can be stored in the flow cytometer. Optical devices using cell recognition techniques can be used to provide the empirical data as feedback to ensure that the probability table is accurate and to adjust the probability table as necessary. In that regard, the self-adhesion of different samples varies, which causes the flow of cells to differ from sample to sample. Feedback from empirical data, in that case, can be very helpful in setting up the probability table. An example of a probability table is given below:

TABLE 2

| Position: | Probability of Event in Current Droplet: | Probability of Event in Previous Droplet: | Probability of Event in Next Droplet: |
| --- | --- | --- | --- |
| 1/16 | 55% | 45% | 0% |
| 2/16 | 75% | 25% | 0% |
| 3/16 | 95% | 5% | 0% |
| 4/16 | 100% | 0% | 0% |
| 5/16 | 100% | 0% | 0% |
| 6/16 | 100% | 0% | 0% |
| 7/16 | 100% | 0% | 0% |
| 8/16 | 100% | 0% | 0% |
| 9/16 | 100% | 0% | 0% |
| 10/16 | 100% | 0% | 0% |
| 11/16 | 100% | 0% | 0% |

As indicated above, the probabilities of an event being located in a particular droplet are based upon the location of the cell 402 in the droplet 400, as illustrated in FIG. 4. Droplet 400 is divided into 16 equal sections. Table 2, above, indicates that the closer the cell 402 is to the breakoff point of the droplet 400, the higher the probability that the cell 402 will not be contained in droplet 400. For example, if the cell 402 is located in region 1, there may be a 55% probability that the cell 402 will be contained in droplet 400. There are also higher resolution calculations that can be made based upon the size of the cell with respect to the droplet and the exact location of the center of the cell 402 based upon the location of the leading and following edges of the cell 402. Of course, calculation of drop probabilities are an optional step and need not be included in the overall process of determining drop desirability.

The droplet probability calculator 212 generates the droplet probability data 214, which is applied to the droplet desirability calculator 216. The droplet desirability calculator 216 combines the event probability data 210 and the droplet probability data 214 to provide the droplet desirability data 218. If there is only a single cell in the droplet, the droplet desirability can be calculated, in accordance with one embodiment, by multiplying the event probability data 210 by the droplet probability data 214. The droplet desirability data generated by this multiplicative process results in a certain purity of the sorted cells.

When more than one cell is present in a droplet, a weighted average of the cells in the droplet can be used to calculate the droplet desirability. For example, if one event has an event probability of 50% and a 100% inclusion rate (droplet probability of inclusion in the drop), and a second event has a 37% event probability and a 55% inclusion droplet probability, the droplet desirability can be calculated as follows:

Droplet Desirability=(50×1.00+37×0.55)/(1.00+0.55)

In this example, the droplet desirability is 45.39%. The droplet desirability number can then be compared to an internally set threshold number. If the droplet desirability number exceeds the internal threshold, a sort decision signal 222 is generated to sort the droplet. The droplet desirability number, as set forth above, results in a certain purity. The droplet desirability number does not necessarily correspond to the purity percentage number. The internal threshold for the droplet desirability is set to correspond to the desired overall purity. Hence, unlike specifying user defined regions, the desirability of a droplet is calculated for sorting. Sorting based strictly upon user defined regions does not always result in a proper sorting decision, as explained above. In that regard, if one droplet contains one cell that is highly desirable and three cells that are not desirable, selection of that drop would probably not be a good decision if a high purity is desired. However, if yield is a primary concern, such as when sorting stem cells, the droplet may have a high desirability and should be selected. Hence, these numbers and the various calculations for selecting a drop for sorting can be adjusted for the particular type of cell being sorted, such as stem cells that occur once every million cells or once every ten million cells. A droplet desirability number of 45% corresponds to approximately a 90% purity for the overlapping Gaussian equations representative of the biological response of bull sperm.

Referring again to FIG. 2, the sort parameter tracker 228 receives the sort decision data 226 and tracks the selection data. The sort parameter tracker 228 accumulates each of the sort decisions and provides a running total of the purity calculation based upon the sort decision data 226. The desirability sort threshold data 230 can be adjusted upwardly or downwardly based upon the purity of the sorts that have been made, as reflected in the sort decision data 226 to provide information to adjust the desirability sort threshold data 230. The purity is predicted by taking the running average of the number of events that have been sorted times the droplet desirability. In the example given above, 1.55 events would have been statistically sorted for predicting purity, since the first event has a 100% inclusion and the second event has a 55% inclusion. In this manner, the sort parameter tracker 228 accumulates each of the sort decisions to continuously adjust the sort parameters. In operation, if a number of events are sorted that are very likely to be in the desirable population that would increase the purity, events with a lower probability would have to be sorted to bring the purity back down. On the other hand, a desired yield can be set with a range of purities to achieve a desired yield, instead of a desired purity. Accordingly, the desirability sort threshold data 230 can be modified so that the sort logic 146 becomes self-tuning. The internal threshold can be automatically raised or lowered to achieve the desired purity based upon changes in the mean ($\mu$) and standard deviation ($\sigma$), or other parameters that are used for other mathematical models. As indicated above, population monitor 206 monitors the event data 144 and generates the model parameters 208 for the event probability calculator 204 based upon the actual event data 144 that is monitored by the population monitor 206. For example, if the model parameters 208 comprise the mean and standard deviation of the two overlapping Gaussian populations, the mean and standard deviation can be adjusted if there is a shift in the event data. In this manner, the sort logic 146 is self-adjusting with respect to shifts in the event data 144. Further, by continuously monitoring the event data 144 using the population monitor 206, error checking and sample monitoring can be achieved. For example, if the event data 144 does not fall within certain preset limits, the flow cytometer can pause the sorting operation and alert the operator that abnormal data has been detected. If the standard deviations are too large and beyond a preset limit, or if the population means for each of the two different overlapping Gaussian populations drift to a value that indicates that the means are too close to each other, an error signal can be generated and the operator can be alerted to intervene.

Finally, the sort decision signal 222, that is generated by sort decision calculator 220, is applied to the timing and charge circuit 224 that properly delays the generation of charge signal 152 to ensure that the proper drop is charged to the correct voltage at the right instant.

By basing sort decisions on a statistical model of a biological sample and, in some cases, instrument performance, numerous benefits are achieved. For example, the flow cytometer becomes easy to use, improves total yield, increases performance, has a more stable performance, and enables self-tuning. With respect to ease of use, an operator of the flow cytometer does not have to manually set gates, test the output and continuously repeat these processes. Usage can now be as simple as entering the desired purity and pressing go. The instrument can then acquire a small amount of data to build an initial model and then proceed with the sorting process. As more data is collected, the model can be continuously updated and self-tuned to become more accurate. In addition, the flow cytometer can track changes in the data over time and tune itself to adjust for those changes. Also, since different samples may provide different results, the flow cytometer can automatically adjust to these differences in the samples, which eliminates the need for the user to re-tune for slight changes.

Further, the accurate results that are provided by the flow cytometer, because of the accurate manner of self-tuning and self-adjustment, results in considerably less wasted sample that occurs during instrument setup and sorts run with improperly set sort criteria, so as to increase overall total yield. Since some samples can be extremely expensive, suboptimal sort results can be very expensive.

Figure 5:
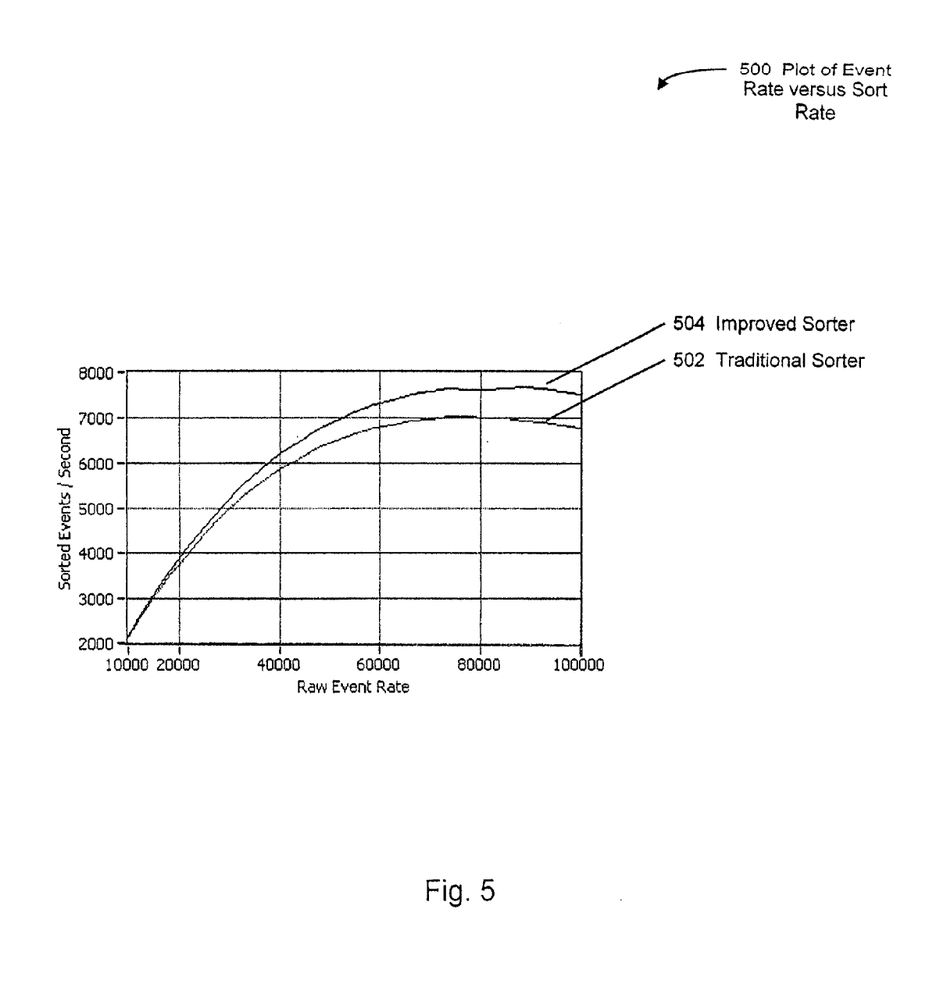
FIG. 5 is a plot of event rate versus sort rate.

FIG. 5 is a graph of a plot 500 of the event rate versus the sort rate for simulated data of a traditional sorter 502 and an improved sorter 504 operated in accordance with the various embodiments disclosed herein. As shown in FIG. 5, instrument sort performance is enhanced by using a mathematical model to make sort decisions, rather than user selected regions. In a typical gated setup that is used by traditional flow cytometers, if multiple events fall in a single droplet and any of those events are outside of the user selected region, even if one of the events is just slightly outside of the user selected region, the entire drop is aborted. Using a mathematical model, such as the statistical model disclosed for two overlapping Gaussian responses, the droplet is analyzed with respect to the overall contribution of the droplet to the yield and purity. In this manner, more droplets are sorted, resulting in increased performance and better yield. In the example plotted in FIG. 5, simulation data is run with the statistical model for bull sperm, with the droplet probability set at 100%. The results of FIG. 5 show an increase in performance of nearly 10% at higher operating speeds. The increase in performance that is illustrated in FIG. 5 may help to achieve faster sorting on existing hardware or make up for performance gaps with alternative technologies. In some applications, very expensive UV lasers are used to achieve acceptable sort performance. However, application of the various embodiments disclosed herein can help lower costs, lower the required power for lasers, etc. For example, 375 nm lasers, which are much less expensive, may be able to achieve acceptable performance using the various techniques disclosed herein. When used in conjunction with optical optimization techniques, such as top hat beam shaping, the performance of the overall system may be able to meet expectations at reduced cost.

In addition, the various embodiments disclosed herein provide a flow cytometer that has performance characteristics that are more stable than traditional flow cytometers. The process of recalculating the model parameters during operation allows the instrument to track changes in the data. Further, the ability to track purity by accumulating the sort decision data allows the desirability sort threshold to be automatically adjusted to ensure that proper purity is achieved.

Since the flow cytometer disclosed in the various embodiments does not sort according to user defined regions, but rather, uses a model for sorting, self-tuning is enabled. The instrument can easily sweep the event rate to achieve an optimal configuration. The user can enter desired parameters, such as desired purity and minimum desired yield, and the instrument can sweep the event rate, while maintaining desired purity until the desired yield is achieved, or is matched as closely as possible. Such processes would result in the highest sort speed possible without requiring the operator to perform dozens of tests to optimize performance.

Other additional optimization processes are also possible using the various embodiments disclosed herein. For example, sweeping the event rate with a set purity, and finding the point where the sort speed multiplied by the yield is maximized, can also be implemented as another optimization process. This point may represent the optimal point for achieving high speed and low loss rates of the sample.

Figure 6:
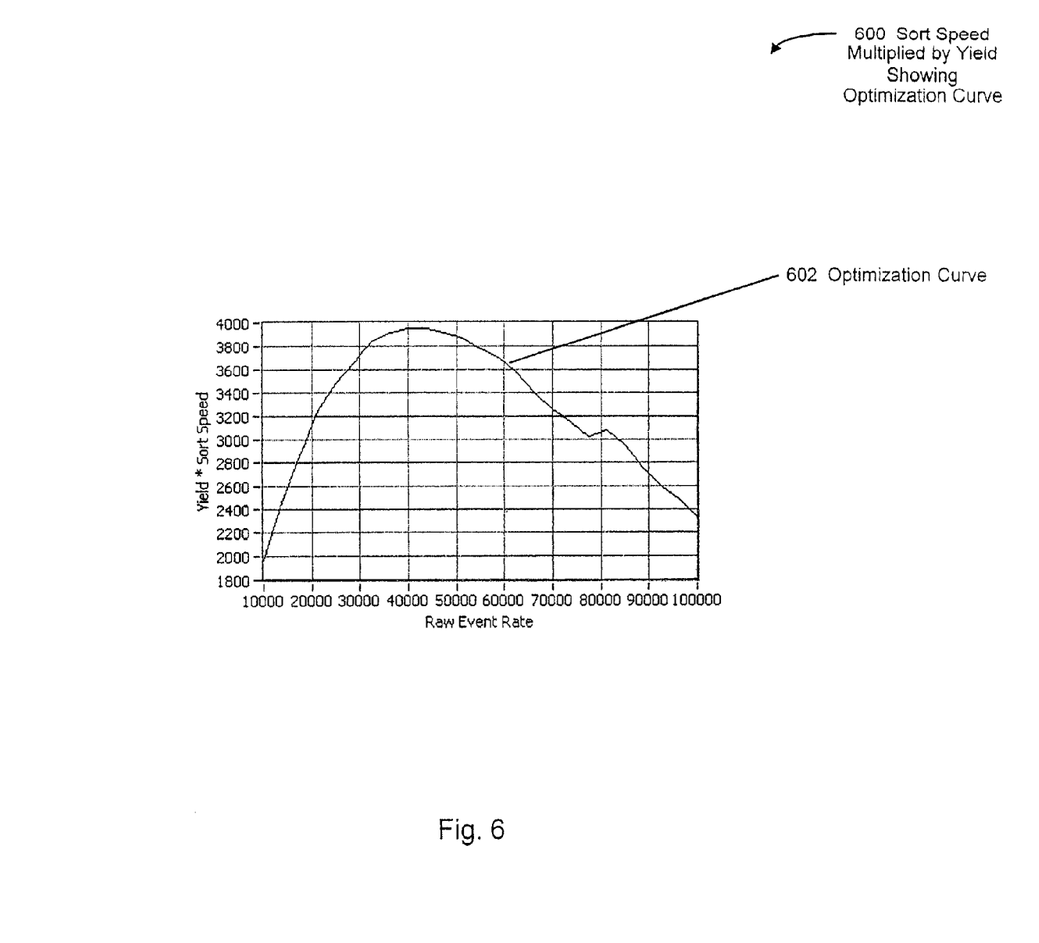
FIG. 6 is a plot of sort speed multiplied by yield showing an optimization curve.

FIG. 6 is a plot, using simulated data, of sort speed multiplied by yield showing an optimization curve 602. As shown in FIG. 6, the optimization curve 602 has a peak at an event rate of approximately 41,000 events per second. Accordingly, 41,000 events per second is the optimal speed for the particular sample shown with reduced sample loss. The optimization curve 602 provides valuable information for sorting applications, since each sample may be slightly different. If generic sort criteria is used, instruments are normally not performing at optimal settings and performance is reduced. By optimizing each instrument for each sample, the full potential of the hardware can be reached and profit from the sorted output can be maximized. In addition, since these functions can be fully automated, no operator interaction is required to achieve these desired results.

Hence, improved sorting ease and performance can be achieved using the various embodiments disclosed herein. Untrained personnel can operate the instrument, reducing operating costs for sort facilities. Performance improvements gained by better statistical modeling and by fully optimizing the processing for each sample increases sort output and profits for the sort facilities. Less wasted sample also results in increased profits for sort facilities.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A method of generating a sort decision signal for sorting a cell of a plurality of cells in a sort logic controller of a flow cytometer comprising:
   calculating statistical event probability data in said sort logic controller of said flow cytometer comprising:
   detecting a biological response of said cell in response to illumination by a source of electromagnetic radiation using optical detectors;
   calculating a statistical probability that said cell belongs to a predetermined population of one of at least two overlapping Gaussian distribution functions based upon analysis of said biological response using an event probability calculator in said sort logic controller comprising;
   deconvolving said two Gaussian distribution functions;
   calculating mean values and standard deviation values for said two Gaussian distribution functions;
   using said mean values and said standard deviation values in a probability distribution function to derive said statistical event probability data for said at least two overlapping Gaussian distribution functions;
   comparing values of said statistical event probability data to determine a most likely population of said at least two overlapping Gaussian distribution functions to which said cell belongs;
   calculating droplet probability data in said sort logic controller comprising:
   determining a location of said cell in a droplet that is formed in said flow cytometer;
   comparing said location of said cell in said droplet with probability data indicating a probability that said cell is present in said predetermined droplet using a droplet probability calculator;
   calculating droplet desirability data for said droplet comprising:
   combining said statistical event probability data and said droplet probability data using a droplet desirability calculator in said sort logic controller of said flow cytometer;
   generating a sort decision signal by comparing said droplet desirability data with an internally set threshold using a sort decision calculator in said sort logic controller of said flow cytometer.

2. The method of claim 1 further comprising:
   tracking said droplet desirability data and said sort decision signal to determine contributions of said plurality of cells to a sorted sample.

3. The method of claim 2 further comprising:
   applying said sort decision signal to a timing and charge circuit.

4. The method of claim 3 wherein said process of sorting said plurality of cells comprises:
   sorting sperm.

5. The method of claim 4 wherein said process of sorting sperm comprises sorting bovine sperm.

6. The method of claim 1 further comprising:
   calculating a probability that said cell belongs to said most likely population by comparing said probability density function of said cell for said most likely population with a maximum probability function calculated with the event location equal to the mean value.

7. The method of claim 6 wherein said process of calculating droplet desirability data comprises:
   calculating said event probability data for each cell present in said droplet;
   calculating a weighted average of said event probability data and said droplet; probability data to generate said droplet desirability data.

8. The method of claim 7 wherein said process of calculating said droplet probability data comprises:
   generating said droplet probability data from empirical data.

9. The method of claim 1 wherein said process of calculating event probability data comprises:
   recalculating said event probability data upon receipt of a selected number of biological responses of said plurality of cells to said illumination of radiation by said source of electromagnetic radiation.

* * * * *